(12) United States Patent
Dopps

(10) Patent No.: US 9,539,077 B1
(45) Date of Patent: Jan. 10, 2017

(54) METHOD FOR ALTERNATIVELY RESISTING AND PERMITTING MENSTRUAL FLOW

(76) Inventor: Daniel A. Dopps, Wichita, KS (US)

( * ) Notice: Subject to any disclaimer, the term of this patent is extended or adjusted under 35 U.S.C. 154(b) by 228 days.

(21) Appl. No.: 13/311,030

(22) Filed: Dec. 5, 2011

(51) Int. Cl.
  *A61F 2/00* (2006.01)
  *A61F 5/44* (2006.01)
  *A61F 13/472* (2006.01)
  *A61B 17/00* (2006.01)

(52) U.S. Cl.
  CPC .............. *A61F 2/0009* (2013.01); *A61F 5/44* (2013.01); *A61F 13/47209* (2013.01); *A61B 2017/0065* (2013.01)

(58) Field of Classification Search
  CPC .................. A61F 13/47209; A61F 13/47227; A61F 13/47263; A61F 13/475; A61F 13/52; A61F 2013/15121; A61F 2013/1513; A61F 2013/15569; A61F 2013/15414; A61F 2013/15382; A61F 2013/16; A61F 2013/47281; A61F 2013/51097; A61F 2013/4729; A61F 2002/7806; A61F 2/0009; A61F 5/44; A61B 2017/0065; A61B 2017/00654; A61B 2017/00641; A61B 2017/00491
  USPC ......................... 604/329, 330, 346, 347, 355, 385.17,604/385.19; 128/898; 602/67
  See application file for complete search history.

(56) References Cited

U.S. PATENT DOCUMENTS

| | | | |
|---|---|---|---|
| 4,542,020 A | 9/1985 | Jackson et al. | |
| 4,699,146 A | 10/1987 | Sieverding | |
| 5,336,208 A * | 8/1994 | Rosenbluth et al. | ......... 604/329 |
| 5,665,477 A | 9/1997 | Meathrel et al. | |
| 5,762,644 A * | 6/1998 | Osborn et al. | ........... 604/385.17 |
| 6,706,276 B2 | 3/2004 | Garg et al. | |
| 6,923,796 B2 | 8/2005 | Bellucci et al. | |
| 7,019,067 B2 | 3/2006 | Holguin et al. | |
| 8,217,219 B2 * | 7/2012 | Shepard | .................. A61F 2/005 424/433 |
| 2003/0120178 A1 | 6/2003 | Heki | |

(Continued)

FOREIGN PATENT DOCUMENTS

| | | |
|---|---|---|
| GB | 2357774 | 4/2001 |
| WO | WO 03/070213 | 8/2003 |

(Continued)

*Primary Examiner* — Howie Matthews
(74) *Attorney, Agent, or Firm* — Kenneth H. Jack; Davis & Jack, L.L.C.

(57) ABSTRACT

A method for controlling menstrual flow including sphincterally contracting and expanding labia minora having left and right labium minuses, such anatomical structures moving to a closed position upon each sphincteral contraction or to an opened position upon each sphincteral expansion; adhering and disjoining the labia minora, each adhesion securing the labia minora at the closed position, the disjunctions freeing the labia minora for opening movement; and resisting and permitting menstrual flow, the resistance occurring on sphincteral contraction and adhesion, and the permission occurring upon sphincteral expansion, each adhering step disposing a hydrophobic and bio-compatible adhesive selected from acrylic adhesives, polyisobutylene adhesives, and silicone adhesives, and each disposition step utilizing an applicator selected from brushes, swabs, rub-on sticks, roll-on applicators, pump sprayers, aerosol sprayers, squeeze tube applicators, bottle applicators, and finger applicators.

6 Claims, 3 Drawing Sheets

(56) References Cited

U.S. PATENT DOCUMENTS

| | | | |
|---|---|---|---|
| 2003/0120225 A1* | 6/2003 | Everhart et al. ............. | 604/285 |
| 2005/0065549 A1 | 3/2005 | Cates et al. | |
| 2010/0121304 A1 | 5/2010 | Zhou et al. | |
| 2010/0152687 A1 | 6/2010 | Carlozzi | |
| 2010/0291058 A1 | 11/2010 | Bowlin et al. | |
| 2010/0297218 A1 | 11/2010 | Gong et al. | |

FOREIGN PATENT DOCUMENTS

| | | |
|---|---|---|
| WO | WO 2009/158584 | 12/2009 |
| WO | WO 2010/111594 | 9/2010 |
| WO | WO 2011/110878 | 9/2011 |

* cited by examiner

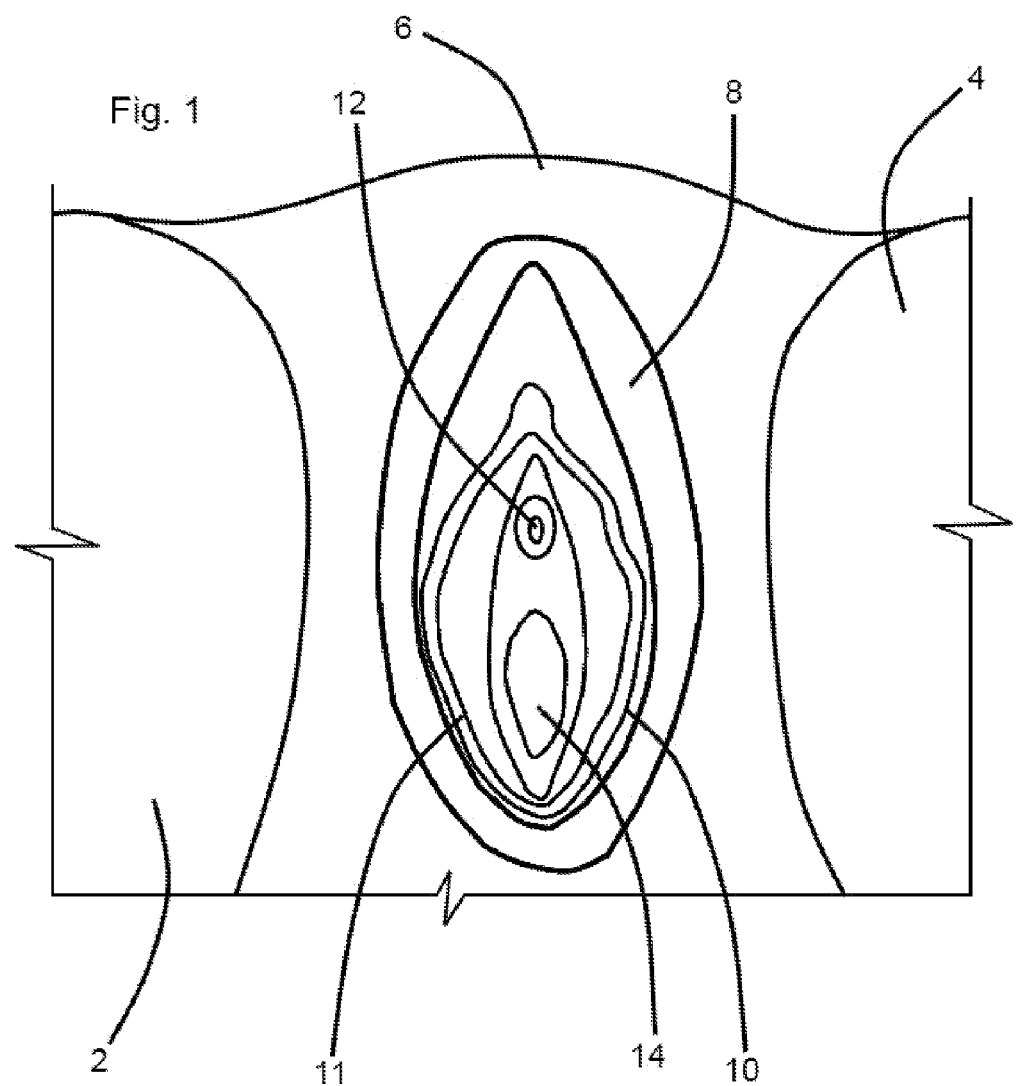

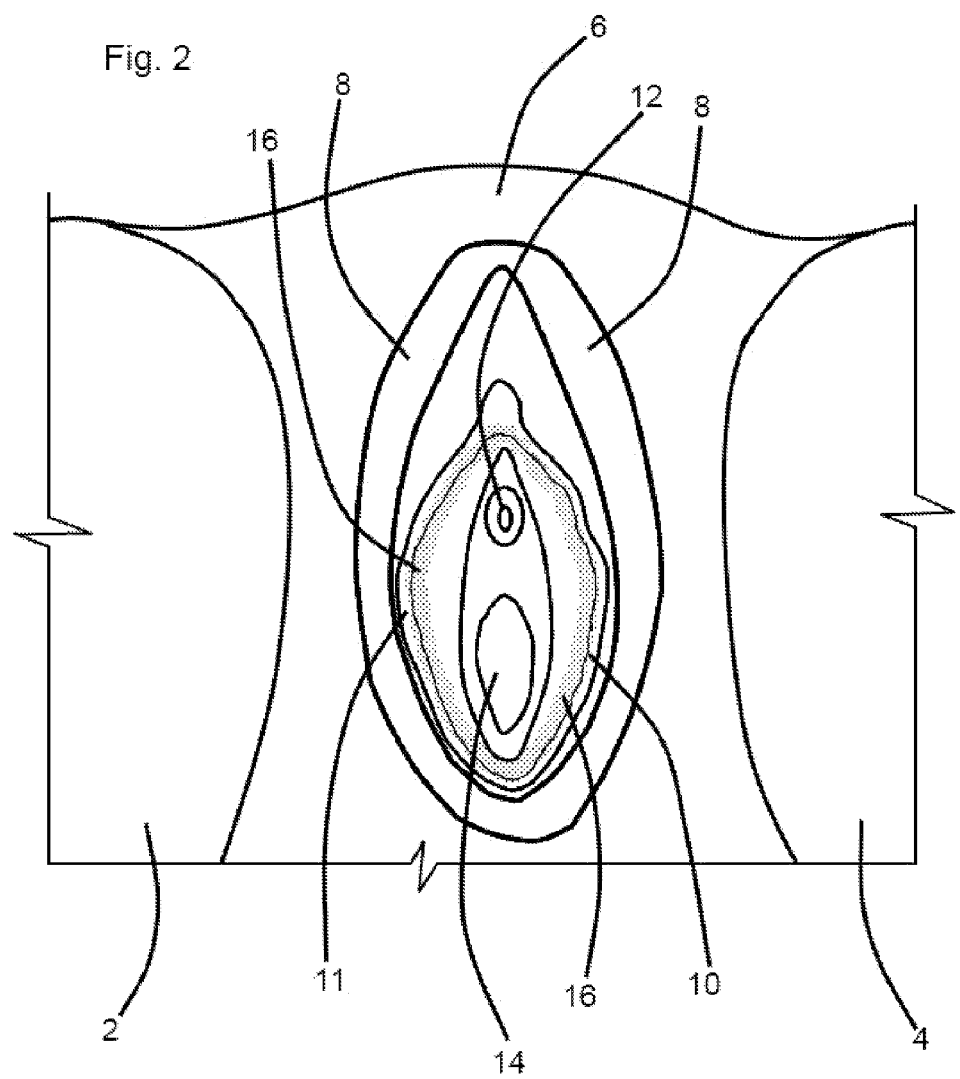

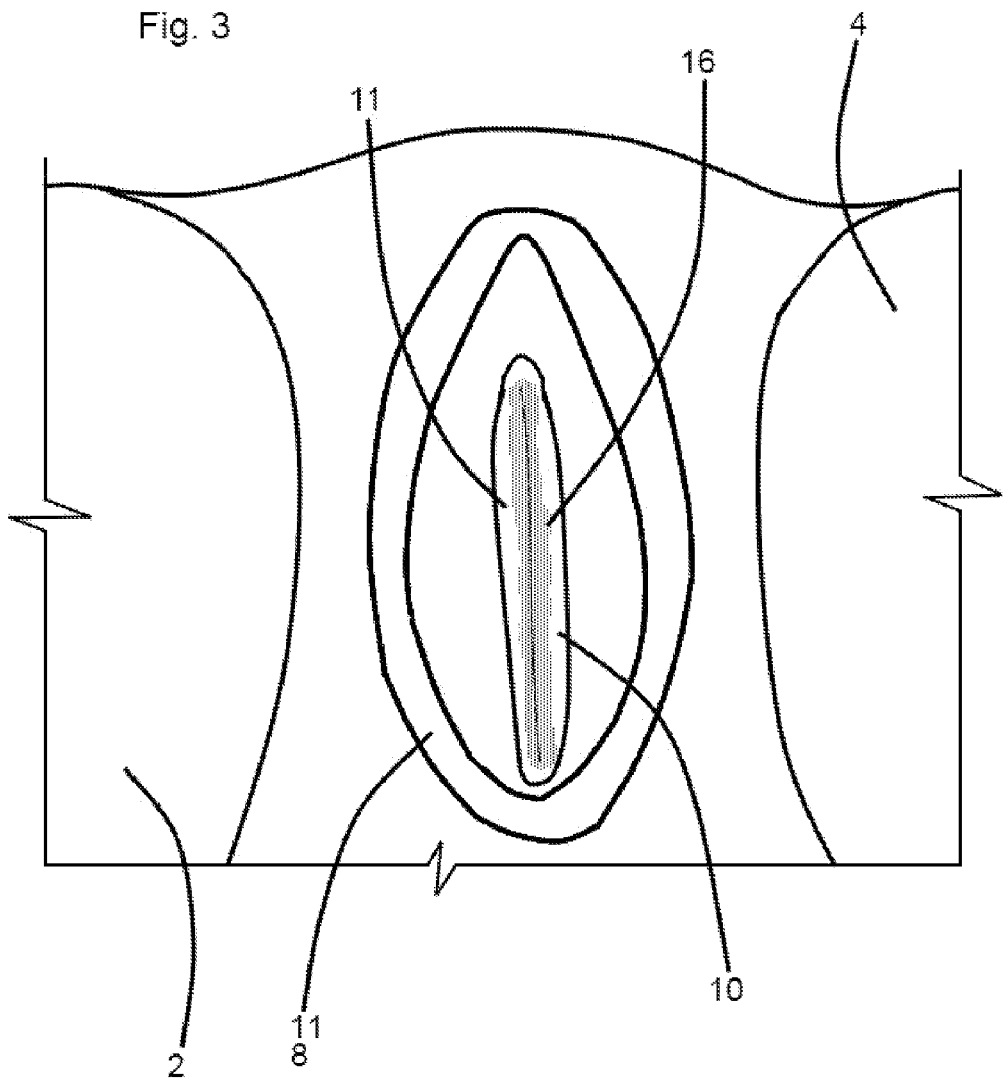

METHOD FOR ALTERNATIVELY RESISTING AND PERMITTING MENSTRUAL FLOW

FIELD OF THE INVENTION

This invention relates to female sanitary hygiene devices, assemblies, processes, and methods. More particularly, this invention relates to such assemblies, processes, and methods which are adapted for temporarily resisting outward bodily emissions of menstrual flow.

BACKGROUND OF THE INVENTION

Biological evolution of mammals has naturally developed various types of vesicles within animal bodies which perform functions of receiving bodily fluids, and alternatively resisting and permitting emissions of the received bodily fluids. A mammal's urinary bladder is an example of such an evolved vesicle, the bladder continually receiving urine from ureters, and periodically purging through voluntary muscle control of the urethral sphincter. In another example, the large intestine analogously functions as such a vesicle for receiving fecal waste and for periodically purging through voluntary muscle control of the rectal sphincter. In another example, evolution of mammals has provided a gall bladder which functions as a vesicle for receiving bile and for, upon hormonal cholecystokinin actuated opening of the sphincter of Oddi, periodically purging the bile into the small intestine for enhanced digestion of fats and oils.

In contrast with the biological evolutionary change which has produced functional fluid receiving and purging vesicles of the types described above, evolution of mammals generally has not functionally associated any such vesicle function with female menstrual flow. Blood emitting from a woman's uterine wall and into the uterus regularly flows outwardly past the cervix which is normally open during menstruation, and then into the vaginal space for typically unrestricted outward passage through the vaginal opening. Unlike other fluids receiving and discharging organs such as the urinary bladder, large intestine and the gall bladder, such vaginal space is not adapted or evolved for alternatively resisting and permitting outward emission or discharge of received menstrual fluids. Yet, according to the dictates and needs of modern life and human society, the existence and functional application of such a vesicle function to menstrual flow would be desirable. The lack of such vesicle function has traditionally been overcome through utilization of tampons and sanitary napkins which are undesirably prone to failures, and which are undesirably expensive and wasteful of resources.

The instant inventive method solves or ameliorates the problems, defects and deficiencies noted above by providing unique adhesives based assembly, method and process steps which attribute or ascribe to a woman's vaginal space enhanced functions in nature of those performed by natural fluids receiving vesicles which are capable of alternatively and through selective voluntary control resisting and permitting outward emissions of fluids.

BRIEF SUMMARY OF THE INVENTION

One of the steps of the instant inventive method for controlling menstrual flow comprises alternatively sphincterally contracting and sphincterally expanding labia minora. In each sphincteral contraction step, the left and right labium minuses which make up the labia minora are moved to a closed and fluids retaining position. Alternatively, in each sphincteral expansion step, such left and right labium minuses are oppositely moved toward an opened and fluid discharging position.

In further and substantially concurrent method steps of the instant inventive method for controlling menstrual flow, the labia minora are alternatively adhered and disjoined. According to the method, each labia minora adhesion step secures the left and right labium minuses at their closed position. Alternatively, performance of each labia minora disjunction step frees the left and right labium minuses for movement toward their opened positions. Each labia minora adhesion advantageously attributes or ascribes to the overlying vaginal space a function in the nature of a vesicle which is capable of retaining biological fluids.

In further and resultant steps of the instant inventive method for controlling menstrual flow, outward discharge of the menstrual flow is alternatively resisted and permitted. Each menstrual flow resisting step advantageously occurs upon a combination of the sphincteral contraction and labia minora adhesion steps, and each such flow resisting step advantageously temporarily stores and accumulates fluid menstrual discharge in the manner of a vesicle. According to the method steps wherein each menstrual flow permitting step occurs upon immediately successive labia minora disjunction and sphincteral expansion steps.

According to the method of the instant inventive, each of the sphincteral contraction and expansion steps is preferably executed via tactile, digital, and frictional forces which are directly applied to the left and right labium minuses for drawing those structures alternatively toward their closed positions and toward their opened positions. In the performance of the instant inventive method, each adhering or adhesion step preferably comprises a disposition of an adhesive upon and about the left and right labium minuses. Since the menstrual flow to be controlled by the instant inventive method is largely water based, the provided adhesive preferably comprises an one having a hydrophobic property. The adhesive which is provided is also necessarily of the type which is bio-compatible with skin, the selected adhesive having a low skin irritation factor, and having a low skin sensitization factor. Classes of adhesives which may be suitably provided comprise silicone adhesives, particularly medical grade silicone gel, acrylic adhesives, polyisobutylene adhesives, and protein/amino acid based adhesives. The selected adhesive also preferably has an appropriate release force characteristic. Where, as is common, the tensile or breaking strength of a user or performer of the method is approximately 17 Newtons per $mm^2$, the selected adhesive, after performance of initial tack and setting steps, should have a release force markedly less than 17 Newtons per $mm^2$.

Adhesive application and transfer means are preferably provided for the performance of the adhesive disposition step of the method. Suitably, direct finger application of the provided adhesive may be performed. Also suitably, commonly known applicators such as brushes, swabs, rub-on sticks, roll on applicators, pump sprayers, aerosol sprayers, squeeze tube applicators, squeeze bottles, absorbent pad applicators, and shake bottle applicators may be utilized.

According to the instant inventive method, a vesicle function is advantageously attributed to the vaginal space overlying the labia minora, such vesicle function advantageously allowing for periodic and voluntarily actuated menstrual discharge, as opposed to continuous and inconvenient menstrual flow.

Accordingly, objects of the instant invention include the adoption and utilization of method steps, as described above, for the performance and achievement of beneficial functions, objectives, and advantages, as described above.

Other and further objects, benefits, and advantages of the instant invention will become known to those skilled in the art upon review of the Detailed Description which follows, and upon review of the appended drawings.

BRIEF DESCRIPTION OF THE DRAWINGS

FIG. 1 is a representational drawing of female genitalia.

FIG. 2 redepicts FIG. 1, the view of FIG. 2 graphically depicting adhesive disposition and sphincteral expansion steps of the instant inventive method.

FIG. 3 redepicts FIG. 2, the view of FIG. 3 representing combined sphincteral contraction and adhering steps of the instant inventive method.

DETAILED DESCRIPTION OF A PREFERRED EMBODIMENT

Referring now to the drawings, and in particular to Drawing FIGS. 1 and 2, a representational view of female genitalia is presented, the view showing right and left legs 2 and 4, mons pubis 6, labia majora 8, urethral opening 12, vaginal opening 14, and labia minora consisting of left and right labium minuses 10 and 11. Such labia minora 10,11 typically consists of visco-elastic epithelial material which is capable of flexibly and elastically moving in the manner of a sphincter in relation to the vaginal opening 14 and in relation to such opening's overlying vaginal space.

Referring simultaneously to FIGS. 2 and 3, in performance of sphincteral contracting steps of the instant inventive method, the left and right labium minuses 10 and 11 are drawn together from the opened position depicted in FIG. 2 to the vaginal space closing position depicted in FIG. 3, the vertically extending structure drawn in FIG. 3 between the left and right labium minuses 10 and 11 being a line. Alternatively, in performance of sphincteral expanding steps of the instant inventive method, opposite motions of the left and right labium minuses 10 and 11 are induced, causing such anatomy being drawn away from each other from the position depicted in FIG. 3 to the position depicted in FIG. 2. In each performance of the sphincteral expanding and sphincteral contracting steps of the instant invention, the opening and closing motion is preferably drawn or induced through direct and tactile finger pressure.

Referring further simultaneously to FIGS. 2 and 3, the instant inventive method for controlling menstrual flow preferably further comprises alternative performance adhering and disjoining steps, each such step being applied to or occurring at the labia minora. In each labia minora adhering step, the left and right labium minuses 10 and 11 are held together at their sphincterally contracted and vaginal space closing positions, as depicted in FIG. 3. Conversely, in each labia minora disjoining step, such anatomical structures are drawn apart through breaking of adhesive bonds to allow motion from the position depicted in FIG. 3 to the position depicted in FIG. 2. In each such step, the tactile finger pressure is preferably utilized for drawing together or apart the left and right labium minuses 10 and 11. Suitably, the sphincteral contraction steps may be induced via drawing legs 2 and 4 together, such action also drawing together the labia majora 8 and the labia minora 10 and 11. Further suitably, an adhesive release agent may be utilized for initiating a sphincteral expansion.

Referring further simultaneously to FIGS. 2 and 3, in further steps of the instant inventive method, an adhesive 16 is disposed about the interior periphery of the left and right labium minuses 10 and 11 so that, upon an execution of one of the sphincteral contracting steps, the left and right labium minuses 10 and 11 may be securely held at their vaginal space closing position.

In a preferred mode of performance of the instant inventive method, the adhesive 16 represents a provision of an adhesive having an hydrophobic character. Suitably, the hydrophobic adhesive may be selected and provided from the group of adhesives consisting of acrylic adhesives, polyisobutylene adhesives, silicone adhesives, and amino acid/protein based adhesives. In order to reduce the risk of skin tearing or contusions, the adhesive preferably has a release force characteristic which is substantially less than the tensile or breaking strength of human skin. Also, in the preferred mode of performance of the instant inventive method, the provided adhesive is bio-compatible, preferably having low skin irritation and low skin sensitization factors.

Disposition of the adhesive 16 may be via fingertip application or, suitably and alternatively, through the use of a common applicator selected from the group of brushes, swabs, rub on sticks, roll on applicators, pump sprayers, aerosol sprayers, squeeze tube applicators, absorbent pad applicators, and bottle applicators.

According to the function of the instant inventive method, upon securing left and right labium minuses 10 and 11, at their closed positions as depicted in FIG. 3 through the skin surfaces connecting action of adhesive 16, the vaginal space overlying the labia minora advantageously functions in the manner of a selectively closed fluid storing vesicle. Selective and voluntary opening of such "vesicle" may be performed according to the steps of the invention through a tactile and finger pressure actuated sphincteral expansion of the labia minora 10,11. Accordingly, through the performance of the method steps of the instant invention, continuous menstrual flow is advantageously converted to a selective and voluntarily actuated vesicle filling and vesicle purging function.

While the principles of the method of the invention have been made clear in the above illustrative embodiment, those skilled in the art may make modifications to the method steps including their identity, character, and sequence of performance without departing from those principles. Accordingly, it is intended that the description and drawings be interpreted as illustrative and not in the limiting sense, and that the invention be given a scope commensurate with the appended claims.

I claim:

1. A method for controlling outward discharge of menstrual flow comprising steps of:
   (a) alternately contracting and expanding labia minora, the labia minora comprising left and right labium minuses wherein the left and right labium minuses have skin surfaces, the left and right labium minuses' skin surfaces moving to a closed position upon each contraction, the movement to the closed position forming a line, said closed position movement positioning the left labium minus at said line, said closed position movement further positioning the right labium minus at said line, and the left and right labium minuses' skin surfaces moving to an opened position upon each expansion, each contraction step and each expansion step comprising a step of application to the left and right labium minuses a drawing force;

(b) alternately performing an adhesive connecting action upon the left and right labium minuses' skin surfaces and disjoining the labia minora, each performance of the adhesive connecting action upon the left and right labium minuses' skin surfaces securing the left and right labium minuses' skin surfaces at the closed position, and each labia minora disjunction freeing the left and right labium minuses' skin surfaces for movement toward the opened position; and (c) alternately resisting and permitting outward discharge of menstrual flow, each such resistance occurring upon one of the performances of the adhesive connecting actions upon the left and right labium minuses' skin surfaces, and each such permission occurring upon one of the labia minora disjunctions the controlling of outward discharge of menstrual flow comprising the alternately resisting and permitting outward discharge of the menstrual flow, wherein each performance of the adhesive connecting action upon the left and right labium minuses' skin surfaces consists of disposition of a liquid or gel adhesive upon the left and right labium minuses' skin surfaces.

2. The method of claim 1 wherein the adhesive disposition step comprises providing an hydrophobic adhesive.

3. The method of claim 2 wherein the adhesive disposition step further comprises provision of a bio-compatible adhesive.

4. The method of claim 2 wherein the adhesive disposition step further comprises providing an adhesive selected from the group consisting of acrylic adhesives, polyisobutylene adhesives, silicone adhesives, and amino acid based adhesives.

5. The method of claim 2 wherein the adhesive disposition step further comprises providing an adhesive having a release force character which is less than the tensile strength of skin.

6. The method of claim 1 wherein each adhesive disposition step comprises providing and utilizing a liquid or gel applicator selected from the group consisting of brushes, swabs, rub-on sticks, roll-on applicators, pump sprayers, aerosol sprayers, squeeze tube applicators, bottle applicators, absorbent pad applicators, and finger applicators.

* * * * *